United States Patent
Sluijter et al.

(10) Patent No.: US 11,806,545 B2
(45) Date of Patent: Nov. 7, 2023

(54) THERAPY OF EYE CONDITIONS WITH PULSED RADIO FREQUENCY

(71) Applicant: Nextep BV, Utrecht (NL)

(72) Inventors: Menno E. Sluijter, Utrecht (NL); Alexandre Jose Leonardo Teixeira, Utrecht (NL)

(73) Assignee: Nextep BV, Utrecht (NL)

( * ) Notice: Subject to any disclaimer, the term of this patent is extended or adjusted under 35 U.S.C. 154(b) by 168 days.

(21) Appl. No.: 17/078,565

(22) Filed: Oct. 23, 2020

(65) Prior Publication Data

US 2022/0126108 A1     Apr. 28, 2022

(51) Int. Cl.
*A61N 1/40*     (2006.01)
*A61N 1/04*     (2006.01)

(52) U.S. Cl.
CPC ............. *A61N 1/40* (2013.01); *A61N 1/0456* (2013.01)

(58) Field of Classification Search
None
See application file for complete search history.

(56) References Cited

U.S. PATENT DOCUMENTS

| | | | |
|---|---|---|---|
| 2008/0077192 A1* | 3/2008 | Harry | A61N 1/0476 42/84 |
| 2010/0198212 A1 | 8/2010 | Sluijter et al. | |
| 2013/0079835 A1 | 3/2013 | Sluijter et al. | |
| 2014/0296948 A1 | 10/2014 | Sluijter | |
| 2017/0354818 A1* | 12/2017 | De Toni | A61N 1/36046 |
| 2020/0101290 A1* | 4/2020 | Rockley | A61N 1/36046 |
| 2020/0171307 A1* | 6/2020 | Rockley | A61N 1/0408 |
| 2021/0022948 A1* | 1/2021 | Musallam | A61K 35/19 |
| 2022/0233848 A1* | 7/2022 | Gad | A61N 1/06 |

FOREIGN PATENT DOCUMENTS

WO     2014083203     6/2014

OTHER PUBLICATIONS wikipedia.org, "Macular Degeneration," accessed Jan. 6, 2023, https://en.wikipedia.org/wiki/Macular_degeneration. (Year: 2023).*

* cited by examiner

*Primary Examiner* — Michael W Kahelin
(74) *Attorney, Agent, or Firm* — Casimir Jones SC; J. Mitchell Jones

(57) ABSTRACT

The present invention relates to a method for medical treatment of a disorder or condition of the eye in a mammal in need thereof, the method comprising applying pulsed radiofrequency (PRF) to the mammal so that there is: an improvement in visual acuity, a stabilization in the decrease of visual acuity, an improvement in contrast of vision, a stabilization in the decrease of contrast of vision, an increase in intensity of color vision, a stabilization in the decrease of color vision, and/or decrease of the blurring of vision and/or a stabilization in the increase thereof.

20 Claims, No Drawings

US 11,806,545 B2

THERAPY OF EYE CONDITIONS WITH PULSED RADIO FREQUENCY

FIELD OF THE INVENTION

The invention relates to the field of medicine, more particularly the field of treatment with electrical signals, more specifically pulsed radio frequency, and even more specifically to the treatment of eye conditions and diseases, such as wet and dry Age related Macular Degeneration (AMD), diabetic retinopathy and glaucoma.

BACKGROUND OF THE INVENTION

In the past few decades this radiofrequency (RF) thermocoagulation has been established as an accepted treatment option for several ailments. The therapeutic effect was mainly concerned with the destruction of tissue by the heat that was generated by the current. The development of a method for administrating high frequency current, pulsed radiofrequency (PRF) allowed using it to treat other pathologies and nerve structures.

With PRF, current is delivered in pulses of short duration (such as 1-50 milliseconds) separated by a silent period of about 0.1 to 0.5 second. Output current may be set not to exceed an equilibrated temperature of 42° C. to prevent cell destruction. Heat generated by the application of the current is dissipated between pulses. Nowadays PRF is recognized as treatment for e.g. various forms of spinal and facial pain and peripheral neuralgias.

International application WO2008/094042A1 by the present inventors shows that PRF has beneficial effects on seeds and the germination of seeds. US patent publication US 2010/0198212 A1 by the present inventors shows that PRF can be used for treatment of joint pain by using a needle-electrode. US patent publication US 2013/0079835 by the present inventors shows that PRF can be used for intravascular medical treatment to boost the immune system and/or relieve pain, optionally together with vaccination. US patent publication US2014/0296948 A1 by one of the present inventors relates to a method of medical treatment of a mammal suffering from cancer by applying PRF before chemotherapy or hormonal therapy either intravascularly or transcutaneously. International publication WO 2014/083203A1 by one of the present inventors and incorporated by reference herein in its entirety relates to irregular PRF signals with a (combined) Poisson distribution of the pulse bursts, preferably in the treatment of pain, cancer, infectious diseases, COPD, depression, sequences of allostatic load, immunosuppression or otherwise caused immunodeficiency. Each of these publications is incorporated by reference herein in its entirety.

SUMMARY OF THE INVENTION

It has now been found that PRF can be used to relieve, improve, stabilize and/or solve conditions and diseases of the eye.

In a first aspect, the present invention embraces a method for medical treatment of a disorder or condition of the eye in a mammal in need thereof, the method comprising applying pulsed radiofrequency (PRF) to the mammal so that there is: an improvement in visual acuity, a stabilization in the decrease of visual acuity, an improvement in contrast of vision, a stabilization in the decrease of contrast of vision, an increase in intensity of color vision, a stabilization in the decrease of color vision, decrease of the blurring of vision and/or a stabilization in the increase thereof.

In other words one or more of the following effects are achieved: i) the visual acuity is either improved or the decrease thereof is stabilized/halted; the contrast of vision is either improved or the decrease thereof is stabilized/halted; the intensity of color vision is either improved or the decrease thereof is stabilized/halted; and iv) the blurring of vision is decreased or the increase thereof is stabilized/halted.

In a second aspect, the present invention embraces a method for medical treatment of age related macular degeneration (dry and wet), glaucoma and/or diabetes retinopathy in a mammal in need thereof comprising: i) applying at least one pair of two skin electrodes, wherein one electrode of said at least one pair of electrodes is placed over an eye and the other electrode of said at least one pair of electrodes is placed on the zygoma area or the suboccipital area; and using a pulse generator to apply pulsed radiofrequency (PRF) over a period of between 5 and 30 minutes, having a peak current output of between 0.6 and 1.5 Ampere; to achieve an improvement in visual acuity, a stabilization in the decrease of visual acuity, an improvement in contrast of vision, a stabilization in the decrease of contrast of vision, an increase in intensity of color vision, a stabilization in the decrease of color vision decrease of the blurring of vision and/or a stabilization in the increase thereof.

The foregoing illustrative summary, other objectives and/or advantages of the present disclosure, and the manner in which the same are accomplished are further explained within the following detailed description.

DETAILED DESCRIPTION

Various aspects and features are herein described. Details are set forth to provide a thorough understanding of the present disclosure. It will be apparent, however, to those having ordinary skill in the art that the disclosed PRF methods may be practiced or performed without some or all of these specific details. As another example, features disclosed as part of one embodiment can be used in another embodiment to yield a further embodiment. Sometimes, well-known aspects have not been described in detail to avoid unnecessarily obscuring the present disclosure. This detailed description is therefore not to be taken in a limiting sense, and it is intended that other embodiments are within the spirit and scope of the present disclosure.

Disorders or Conditions

Oxidative stress and chronic inflammation are several of the hallmarks of many eye diseases. The present inventors have found PRF to have an effect in correcting these abnormal responses and have found that it therefore can be used for treatment of other eye conditions.

In one preferred embodiment, said eye disorder or condition is retinal disorder or condition, or optic neuropathy.

Examples of retinal disorders or conditions that can be treated with the present method are the following: age related dry macular degeneration, age related wet macular degeneration, diabetes retinopathy, macular edema (of any cause), diabetic macular edema and retinal vein occlusion (macular edema).

An example of optic neuropathy that can be treated with the present method is glaucoma.

Method of Application of PRF

In some preferred embodiments, PRF is applied locally or regionally to the eye. This can be done transcutaneously or invasively.

In transcutaneous application, preferably self-adhesive, skin electrodes are attached to the skin. The purpose of transcutaneous application is to generate equal electric fields in a tissue compartment. The peak current that is required to achieve that is calculated first. Next, skin electrodes are attached to the skin. It may be envisaged that these skin electrodes have a surface ranging from 10 cm$^2$ to 120 cm$^2$. The size of the skin electrodes to be used depends on the peak current that has been calculated. Each cm$^2$ of the skin electrodes can transport a maximum of 25 mA of peak current, assuming a duty load of 15 milliseconds/s. In local application the electrodes are placed on the head and/or neck area of the mammal to be treated, preferably near or over the eye.

In invasive application one or more electrodes are used that enter into the mammal body. In such an embodiment, the method further comprises inserting a needle or other invasive device into the body, e.g. into or close to the eye. In case of invasive application of the PRF, this may be by interstitial or intravitreal application of a needle or other device that can apply the pulsed radiofrequency. An example of such an electrode is a needle-electrode or other invasive device. Ophthalmologists might use that option, since they are familiar with techniques of injection into or close to the eye; but should be used with care since the eye is a very sensitive organ. Such injection techniques can be combined with a PRF treatment by connecting a suitable needle to a PRF generator. Since the tip of the needle is not far from the retina and since the required electric fields are so low voltages of 12-15 V will probably suffice to generate a biological effect. When short 27G needles are used insulation is unnecessary.

US 2010/0198212 A1 of the present inventors and incorporated by reference herein in its entirety shows the use of a specific electrode for invasive application of PRF, e.g. by a completely insulated outer needle electrode with a sharp tip, a removable stylet, and one or more conductive, blunt ended, optionally flexible electrodes, optionally with an insulated tip. This publication is incorporated by reference herein in its entirety.

In some preferred embodiments, PRF is applied systemically. This can for example be done transcutaneously, by attaching, preferably self-adhesive, skin electrodes to the skin. It may be envisaged that these skin electrodes have a surface ranging from 25 cm$^2$ to 120 cm$^2$. In systemic application the electrodes are placed on a body part that need not be close to the eye, e.g. on the arms and/or legs or torso. In systemic application PRF effects a change to the behaviour of all immune cells in the mammalian body.

In some preferred embodiments, PRF is applied transcutaneously after positioning at least one pair of two skin electrodes on the mammal to be treated. Since PRF is a current, a closed circuit or loop is required for the method to work. For this one or more pairs of electrodes are used. Each pair consists of two electrodes, one electrode which functions as an active electrode sending the current and one electrode which functions as a referral electrode receiving the current. It should be noted that two of the same type of electrodes may be used which can each carry out both functions.

In some preferred embodiments wherein PRF is applied locally and transcutaneously, one electrode of each pair of electrodes is placed over the eye. In case only one pair of electrodes is used, one (the active) electrode is placed over the eye (e.g. covering the eyelid only or the eyelid and surrounding area), being the point of entry of the current into the mammal to be treated. The other remaining electrode (functioning as the referral electrode) may for example be placed on another part of the head or on the neck of the mammal, such as on the zygoma area or on the suboccipital area. In order to obtain the best effect and to be efficient it is important that the current travels through the complete eye. This can be obtained by careful placement of the active electrode (over or near the eye) and the referral electrode (over the zygoma area or on the suboccipital area).

In another preferred embodiment both electrodes of the at least one pair of electrodes are placed on either side of the head (near the temple/zygoma area). In this embodiment there is no electrode placed over the eye. This is an example or regional treatment.

It may be advantageous to have a second pair of electrodes, for example to treat both eyes at the same time. In that case one electrode (functioning as active electrode) of a first pair is placed over one eye and one electrode (functioning as active electrode) of a second pair is placed over the other eye.

In a particularly preferred embodiment, said mammal to be treated is a human.

Pulsed Radiofrequency

Pulsed radiofrequency is the technique whereby radio frequency (RF) oscillations are gated at a rate of pulses (cycles) per second (one cycle per second is known as a hertz (Hz)). In other words, pulsed radiofrequency is an electrical signal consisting of current pulses in a radiofrequency range, for example the range of 80 KHz to 10 MHz.

PRF is a clinically proven method to alleviate pain in cases where pain sensation is due to the presence of a nociceptive focus (such as in case of pain caused by pinching a nerve by a slipped disc of the spinal column, facial pain, trauma, etc.). PRF works through applying an electrical AC current to the vicinity of the nociceptive focus. The small magnetic component of the current then causes a recombination of radical pairs, thus (partially) reverting the overproduction of oxygen radicals that is the hallmark of oxidative stress (Brasil L J, Marroni N, Schemitt E, Colares J. Effects of Pulsed Radiofrequency on a Standard Model of Muscle Injury in Rats, Anesth Pain Med. Online ahead of Print; 10(1):e97372. doi: 10.5812/aapm.97372)

In some preferred embodiments, the PRF is applied over a period of between 0.5 and 60 minutes, or between 5 and 30 minutes, preferably between 10 and 20 minutes. In a specific embodiment, PRF is applied during 15 minutes.

In some preferred embodiments, the PRF pulses are delivered with a frequency of between 1 Hertz and 20 Hertz, preferably between 2 and 10 Hertz.

In some preferred embodiments, the PRF pulses are delivered with a pulse duration of between 1 millisecond and 100 milliseconds, such as between 1 and 20 milliseconds. Pulses are separated by a rest phase (also called silent period), that depends on the pulse duration and the frequency. This rest phase depends om the pulse frequency and on the pulse width (pulse duration) that have been selected. During this rest phase the voltage may be either completely turned down to 0 V or it may be significantly reduced.

In some preferred embodiments, the PRF pulses are delivered with an average duty load not exceeding 18 millisecond per second, such as when using irregular PRF. In an embodiment, the PRF pulses are delivered with an average duty load not exceeding 15 millisecond per second, such as when using regular PRF. The duty load can be calculated by multiplying the (average) pulse duration with the number of pulses per second (=pulse frequency).

PRF may be applied using regular pulses or irregular pulses. More information regarding these pulses can be found in the patent publications of the present inventor(s) disclosed above that are incorporated by reference herein. With regular pulses is meant a fixed duration for each pulse and a fixed pulse frequency. With irregular pulses is meant a varying pulse duration and a varying pulse frequency.

In some preferred embodiments, the PRF comprises regular pulses each with a single frequency and with a single pulse duration. An example thereof is a pulse duration of 5 milliseconds at a frequency of 3 Hz, leading to a duty load of 15 milliseconds per second.

In some preferred embodiments, the PRF comprises irregular pulses with an average pulse duration of between 1 and 10 milliseconds, such as 2.89 milliseconds, and an average frequency of between 1 and 20 Hz, such as 5.11 Hz. An irregular signal according to the present invention—in one embodiment—is defined as a PRF signal wherein the pulses are fired according to a Poisson distribution or a combination of Poisson distributions. See also WO 2014/083203A1 as discussed above.

In some preferred embodiments, the PRF are delivered by an electrode with an impedance of less than 1000Ω. Impedance in tissue is small; this maximum value is coming from transition from electrode to skin and depends significantly on the type/manufacturer of the electrodes used.

In some preferred embodiments, the PRF is an electrical signal having an peak current output of between 0.2 and 2.0 Amperes, such as between 0.6 and 1.5 Amperes. It should be noted that the peak current output differs from the mean current output in case of irregular pulses and also differs from transcutaneous and invasive application and from local/regional to systemic application. When using transcutaneous application it is the purpose to initiate electric fields in the magnitude that cells use for intercellular communication, the so-called physiological range (50-250 V/m) throughout the tissue compartment that is treated. At this low level cell damage due to electric fields is not possible. It is only when the electric fields are in the so-called electroporation range (10000-13500 V/m) or higher that cell damage becomes an issue. Since RF currents have a tendency to spread the current has to be calculated based on the amount of spreading that is allowed by the anatomy. It is then preferred to have a current density of 75-90 A/m².

The instruments for transcutaneous application of PRF to a patient generally comprise two electrodes, connected to a PRF current source. The two electrodes, both attached to the skin of the mammal to be treated establish an electrical circuit. The procedure to apply transcutaneous PRF is easy to perform and does not need special skills. A pair of skin electrodes (preferably self-adhesive) are applied to the skin of the mammal to be treated. The "Spring2", a pulsed radiofrequency generator and its skin electrodes are developed and sold by Springlife Medical (www.springlife.com).

The PRF treatment is painless (except for the initial insertion of the needle electrode) and no serious and lasting adverse reactions have thus far been observed. In otherwise healthy persons no apparent changes take place.

Other variations of the disclosed embodiments can be understood and effected by those of ordinary skill in the art in practicing the present invention by studying the drawings, the disclosure, and the appended claims. In the claims, the word "comprising" does not exclude other elements or steps, and the indefinite article "a" or "an" does not exclude a plurality. Unless otherwise specified, numerical ranges are intended to include the endpoints.

It is within the scope of this disclosure for one or more of the terms "substantially," "about," "approximately," and/or the like, to qualify each adjective and adverb of the foregoing disclosure, to provide a broad disclosure. As an example, it is believed those of ordinary skill in the art will readily understand that, in different implementations of the features of this disclosure, reasonably different engineering tolerances, precision, and/or accuracy may be applicable and suitable for obtaining the desired result. Accordingly, it is believed those of ordinary skill will readily understand usage herein of the terms such as "substantially," "about," "approximately," and the like.

The use of the term "and/or" includes any and all combinations of one or more of the associated listed items. Unless otherwise noted, specific terms have been used in a generic and descriptive sense and not for purposes of limitation. The invention is further elucidated by the following non-limiting examples.

EXAMPLES

The following examples show report of the transcutaneous use of PRF on the eye of four patients with several different eye conditions or diseases. The following materials and methods were used: a "Spring2" prototype pulsed radiofrequency generator and its skin electrodes (having a size of 5.5 cm×5.5 cm), developed and sold by Springlife Medical (on the world wide web at springlife.com). A pulse duration of 5 milliseconds and a frequency of 3 Hertz was used in regular phase. The duration of treatment was 15 minutes.

Example 1

Patient 1

The patient is a 93 years old male, with severe age-related macular disease. This patent used to be an artist painter that stopped this activity two years before his PRF treatment due to a substantially decreased vision acuity and loss of color discrimination, which did no longer enabled him to paint. Prior to the PRF treatment, he had been treated with intravitreal injections and this line of treatment was abandoned after 6 months of monthly treatments without any improvement.

He received PRF on on both eyes; two pair or electrodes were placed over the eyelids (active electrodes) and the suboccipital area (referral electrodes). A current of 1.5 Amperes was applied. The effects were immediate and stunning; a significantly increased visual acuity and color discrimination that resulting in the patient resuming painting the very same night, leading to excellent quality paintings. The results remained for two years.

Example 2

Patient 2

The patient is a 73 years old male, with severe diabetic retinopathy of the right eye, the left eye was enucleated two years prior due to complications following eye surgery. He has been on treatment with intravitreal injections for the last 4 years but the symptomatology was aggravating and during each of the Optic Coherence Tomograms (OCTs) he received there were signs of macular edema.

He received initially received two PRF treatments about one month apart on his right eye. After the first PRF treatment, a significant improvement in visual acuity was reported by the patient. After the second PRF treatment the patient reported less improvement compared to the first treatment. Two months after the second treatment. an OCT was carried out in which there no longer was any sign of macular edema.

Several months later, the patient received an intravitreal injection and after that treatment an OCT was carried out in which there was still no sign of macular edema. An ophthalmologist reported that the vision was stable and that the patient is satisfied with the present situation as a result of the PRF treatment.

The patent then received another PRF treatment after which there was an immediate additional improvement of the blurring of vision and visual acuity. All treatments were done with the electrodes applied over the eyelid of the treated eye and over the zygoma on the same side. A current of 0.68 Amperes was applied.

Before the PRF the patient drew 4 letters 1 cm high and 1 cm wide to explain his major complaint: the middle letters couldn't be seen, they merged and the image was blurred. Immediately after the PRF-treatment, he spontaneously tried to read the previously drawn letters that he could now see without difficulty and no merging or blurring. Next, he spontaneously drew a row of letters 0.5 cm high×0.5 cm wide and he could see the middle letters without any trouble. The vision acuity improved 1 line. Two days and 8 days after the procedure he referred on a telephone interview that this improvement was vanished, so the effect in this patient was short but still present.

Example 3

Patient 3

The patient is a 79 years old woman with age related macular disease with a deterioration in vision over the previous 3 months to the right eye to such an extent that she had trouble driving a car.

She received PRF treatment on her right eye. The electrodes were applied over the eyelid of the treated eye and over the zygoma on the same side. A current of 0.77 Amperes was applied. The vision after the treatment was greatly increased with a much clearer vision and no longer any trouble driving a car.

Approximately two months later, she received PRF treatment on her left eye. The electrodes were applied over the eyelid of the treated eye and over the zygoma on the same side. A current of 0.77 Amperes was applied. Prior to the treatment the visual acuity on the right eye was 20/30 and on the left 24/40. Immediately after the procedure (<5 minutes) the visual acuity on the right eye was the same 20/30 while the left eye improved 2 lines to 20/25. She also referred on the next day, that the vision was more clear, the contours more sharp and the left eye fells much lighter, before she says that she had a feeling of heaviness on the left eye. On the 4th day these improvements remain. The improvement is maintained till the present.

Example 4

Patient 4

The patient was a 93-year old woman with age-related macular disease. She could see very little with her left eye; on her right eye, she was blind. For the PRF treatment, both electrodes were placed on either side of the head, over the temple area. A current of 1.4 Amperes was applied. A few days after the treatment there was a significant improvement of vision. She could find items in the house and she could identify the colors of paintings. After approximately two weeks her acuity slowly decreased. Besides the effect on her eye, her mood and memory functions also improved. She was treated for the second time about two weeks later. Immediately after the treatment, there was again a significant improvement. After years she walked freely through the house holding cup and saucer without any problems. Just as the first time, there was an improvement of mood and memory functions.

Example 5

Patient 5

The patient was a 87-year old female with wet age-related macular disease. She was treated with two electrodes on either side of the head with irregular PRF. A current of 0.6 Amperes was applied. After approximately 36 hours her vision significantly improved. She had two blind spots in her vision that disappeared after treatment. Also, after treatment she could see the subtitles on the TV again. In total she had two treatments. After each treatment vision improved more.

We claim:

1. A method for medical treatment of a disorder or condition of the eye in a mammal in need thereof, the method comprising applying pulsed radiofrequency (PRF), with a duty load not exceeding 18 ms/s, in the range of 80 KHz to 10 MHz to the mammal so that an outcome selected from the group consisting of an improvement in visual acuity, a stabilization in the decrease of visual acuity, an improvement in contrast of vision, a stabilization in the decrease of contrast of vision, an increase in intensity of color vision, a stabilization in the decrease of color vision, decrease of the blurring of vision and a stabilization in the increase of the blurring in vision is achieved.

2. The method according to claim 1, wherein said eye disorder or condition is selected from the group consisting of a retinal disorder or condition and an optic neuropathy.

3. The method according to claim 2, wherein said retinal disorder or condition is selected from the group consisting of age related dry macular degeneration, age related wet macular degeneration, diabetic retinopathy, macular edema, diabetic macular edema, and retinal vein occlusion.

4. The method according to claim 2, wherein said optic neuropathy is glaucoma.

5. The method of claim 1, wherein said pulsed radiofrequency is applied locally to the eye.

6. The method of claim 5, wherein said pulsed radiofrequency is applied transcutaneously or invasively.

7. The method of claim 1, wherein said pulsed radiofrequency is applied systemically.

8. The method of claim 7, wherein said pulsed radiofrequency is applied transcutaneously.

9. The method according to claim 1, wherein said pulsed radiofrequency is applied transcutaneously after positioning at least one pair of two skin electrodes on the mammal to be treated.

10. The method according to claim 5, wherein said pulsed radiofrequency is applied transcutaneously after positioning at least one pair of two skin electrodes on the mammal to be treated, wherein one electrode of said at least one pair of electrodes is placed over the eye.

11. The method according to claim 9, wherein the other electrode of said at least one pair of electrodes is placed on another part of the head or on the neck of the mammal.

12. The method according to claim 11, wherein the other electrode is placed on the zygoma area or on the suboccipital area.

13. The method according to claim 1, wherein said pulsed radiofrequency is applied transcutaneously after positioning two pair of two skin electrodes on the mammal to be treated, wherein one electrode of each of said two pairs of electrodes are placed over both eyes.

14. The method according to claim 6, wherein said invasive application is selected from the group consisting of interstitial and intravitreal application of a needle or other device that can apply the pulsed radiofrequency.

15. The method according to claim 1, wherein the PRF are applied over a period of between 0.5 and 60 minutes.

16. The method according to claim 1, wherein the PRF is an electrical signal consisting of current pulses in a radiofrequency range.

17. The method according to claim 1, wherein the PRF is an electrical signal consisting of irregular pulses with an average pulse duration of 2.89 milliseconds and an average frequency of 5.11 Hz.

18. The method according to claim 1, wherein the PRF is an electrical signal having a peak current output of between 0.4 and 1.5 Ampere.

19. The method according to claim 1, where the mammal is a human.

20. A method of medical treatment of age related macular degeneration (dry and wet), glaucoma and/or diabetes retinopathy in a mammal in need thereof comprising applying at least one pair of two skin electrodes, wherein one electrode of said at least one pair of electrodes is placed over an eyes and the other electrode of said at least one pair of electrodes is placed on the zygoma area or the suboccipital area;

using a pulse generator to apply pulsed radiofrequency (PRF), with a duty load not exceeding 18 ms/s, in the range of 80 KHz to 10 MHz over a period of between 5 and 30 minutes, having a peak current output of between 0.6 and 1.5 Ampere;

wherein said application of said PRF results in an outcome selected from the group consisting of an improvement in visual acuity, a stabilization in the decrease of visual acuity, an improvement in contrast of vision, a stabilization in the decrease of contrast of vision, an increase in intensity of color vision, a stabilization in the decrease of color vision and a decrease of the blurring of vision.

* * * * *